United States Patent [19]

Abernathy et al.

[11] Patent Number: 4,622,049
[45] Date of Patent: Nov. 11, 1986

[54] APPARATUS FOR ADJUSTING AND MAINTAINING THE HUMIDITY OF GAS AT A CONSTANT VALUE WITHIN A CLOSED SYSTEM

[75] Inventors: Bethel R. Abernathy, Franklin; Ronald R. Walters, Germantown, both of Ohio

[73] Assignee: The United States of America as represented by the United States Department of Energy, Washington, D.C.

[21] Appl. No.: 762,369

[22] Filed: Aug. 5, 1985

[51] Int. Cl.[4] ............................................. G01N 17/00
[52] U.S. Cl. ................... 55/250; 261/119 R; 73/865.6
[58] Field of Search ............. 55/250, 251; 261/119 R; 73/432 SD

[56] References Cited

U.S. PATENT DOCUMENTS

| | | | |
|---|---|---|---|
| 1,877,888 | 9/1932 | Reichert et al. | 55/250 |
| 2,589,111 | 3/1952 | Mills | 55/250 |
| 3,063,220 | 11/1962 | Almquist | 55/250 |
| 3,319,298 | 4/1967 | Schreiber | 261/119 R |
| 3,488,681 | 1/1970 | Mita et al. | 73/432 SD |
| 3,505,989 | 4/1970 | Truhan . | |
| 3,714,833 | 2/1973 | Newman | 73/432 SD |
| 3,886,791 | 6/1975 | Grossman | 73/432 SD |
| 3,977,091 | 8/1976 | Hortig et al. . | |
| 4,406,843 | 9/1983 | Nakamura et al. | 261/22 |
| 4,435,025 | 3/1984 | Weintraub . | |

Primary Examiner—Tim Miles
Attorney, Agent, or Firm—James H. Chafin; Albert Sopp; Judson R. Hightower

[57] ABSTRACT

The humidity of a gas within a closed system is maintained at constant level by providing a saturated salt solution within a lower chamber in communication with an upper chamber conjointly defined by upper and lower container sections in sealing contact with each other to establish a closed container. A partition wall separates the salt solution from the test region in the upper chamber. A tube extending through the partition plate allows humidified gas to pass from the lower to the upper chamber. A glass wool plug or membranous material within the tube prevents migration of salt into the test region.

10 Claims, 3 Drawing Figures

4,622,049

APPARATUS FOR ADJUSTING AND MAINTAINING THE HUMIDITY OF GAS AT A CONSTANT VALUE WITHIN A CLOSED SYSTEM

The U.S. Government has rights in this invention pursuant to Contract Number DE-AC04-76DP00053 between the U.S. Department of Energy and Monsanto Research Corporation.

BACKGROUND OF THE INVENTION

The present invention relates generally to apparatus for adjusting the relative humidity of gas to a fixed value and, more particularly, to apparatus for maintaining and controlling humidity and moisture levels at constant values within small volume closed containers.

Systems utilizing saturated aqueous salt solutions for controlling and maintaining humidity of a gas within a closed space are known. These systems have numerous applications, such as in conducting long-term (e.g., two years) compatibility tests of materials. For example, it may be desirable to determine whether two dissimilar metals, joined together in a mechanism, experience corrosion when exposed to moisture within an operating environment.

In conducting material compatibility tests, it is important that humidity be kept at a constant value, meaning that pressure and ambient temperature of humidified gas must be precisely controlled. Also, since these material compatibility tests are of long-term duration, it is preferable to employ a testing system wherein the saturated salt solution does not have to be replenished, as would be required in the humdifier disclosed in U.S. Pat. No. 4,406,843 to Nakamura et al.

Of particular importance when conducting compatibility tests is the exclusion of solids, such as salt particles, from the immediate test environment. In less desirable humidification devices utilizing saturated salt solutions as a vapor source, problems have occurred in long-term testing due to migration of the salts. Somehow these salts migrate from the bottom of a test container, up the container side walls, and into the environmental test region. Obviously, the presence of salt particles and other undesirable substances within the test region tends to cause corrosion of test materials, destroying the validity of the tests.

SUMMARY OF THE INVENTION

It is accordingly one object of the present invention to provide a method and apparatus for easily maintaining and controlling the humidity of gas at a constant value.

Another object of the invention is to provide a method and apparatus for conducting long-term material compatibility tests under conditions of controlled levels of humidity and ambient temperature.

Still a further object is to control humidity levels with a saturated aqueous salt solution within a closed system that does not require replenishment of solution during the testing process.

Still a further object is to provide apparatus preventing migration of salt particles from the saturated aqueous solution into the testing region.

Still a further object is to provide apparatus that can be used to conduct material compatibility tests on the order of years with minimal maintenance.

Additional objects, advantages and novel features of the invention will be set forth in detail in part in the description which follows and in part will become apparent to those skilled in the art upon examination of the drawings, or may be learned by practice of the invention. The objects and advantages of the invention may be realized and obtained by means of the instrumentalities and combinations particularly pointed out in the appended claims.

An improved device for maintaining and controlling the humidity of a gas within a sealed environment comprises, in accordance with the invention, a container having a partition for separating the interior of the container into upper and lower chambers. The lower chamber contains an aqueous saturated salt solution. The upper chamber establishes a test region within which material compatibility tests may be conducted. A tube extends through the partition plate to provide communication between the upper and lower chambers and to enable gas humidified by the salt solution within the lower chamber to pass into the upper chamber. A filtering medium disposed within the tube allows humidified gas to enter the upper chamber while preventing migration of salt particles from the lower to the upper chamber.

The tube preferably extends below the lower surface of the partition plate so that the lower end of the tube is located below the partition plate and above the surface of the salt solution. Location of the tube lower end between the plate and solution increases the migration path of salts so that the likelihood of salt particles traveling up side walls of the container, across the lower surface of the partition plate, down along side walls of the tube into the bottom opening thereof for entrance into the test environment, is virtually zero.

The test region may be formed within a first container constituting a bell-shaped jar or other container open at the bottom. The solution may be stored within a second container open at the top for mating engagement with the bottom of the first container through sealing flanges. The second container includes the partition plate with the tube projecting upward therefrom. The tube can also be used to pour saturated aqueous salt solution into the lower container.

In accordance with the method of the present invention, the saturated salt solution is first poured into the second container, an upper surface of which is then wiped to remove any stray salt or liquid spilled thereon. A filter material is then inserted into the tube. The first container is then mounted in sealing contact to the second container to establish the test region sealed from ambient environment and communicating with the solution through the filter. The test region is then exposed to ambient atmosphere while the device is heated to desired temperature. Humidity increases to a required level in the first container as the salt solution releases water vapor. Exposure of the test region to ambient atmosphere prevents build-up of pressure within the test region at the desired temperature which may be different from ambient temperature. The test region is then sealed when the required humidity level is reached. Constant humidity is maintained within the closed system with subsequent minimal effort and monitoring.

DETAILED DESCRIPTION OF THE INVENTION

Figure 1:
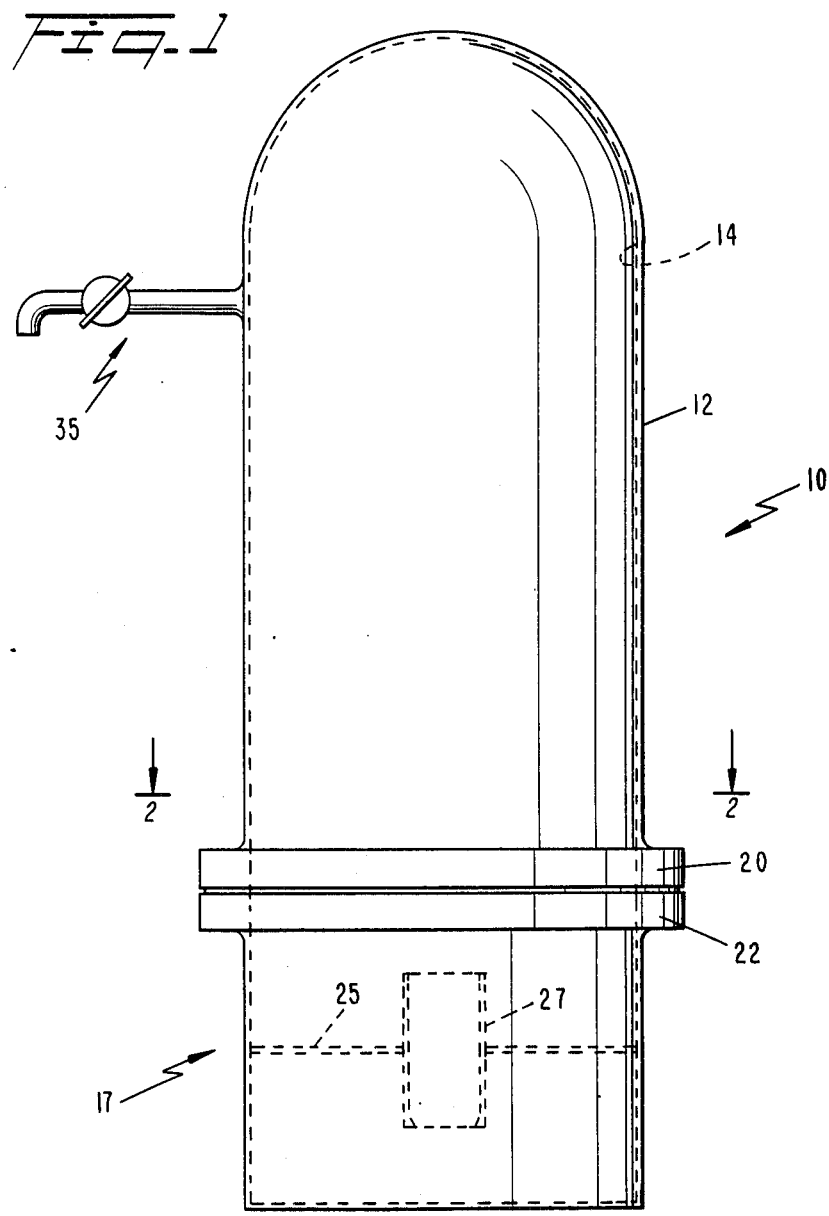
FIG. 1 is a side view of an improved humidification device for adjusting the humidity of gas according to the present invention.
Figure 2:
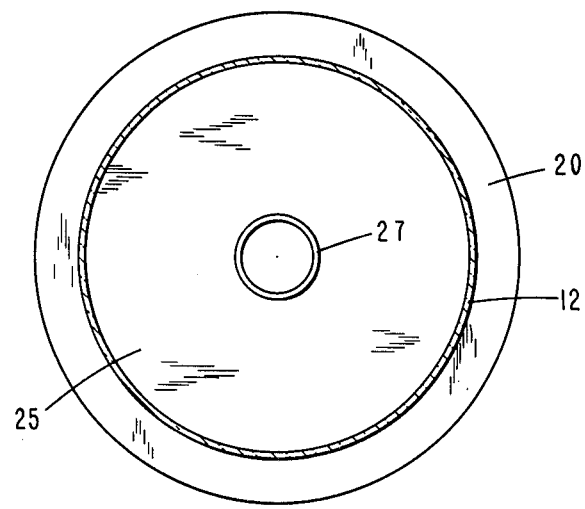
FIG. 2 is a sectional view taken along the line 2—2 of FIG. 1.
Figure 3:
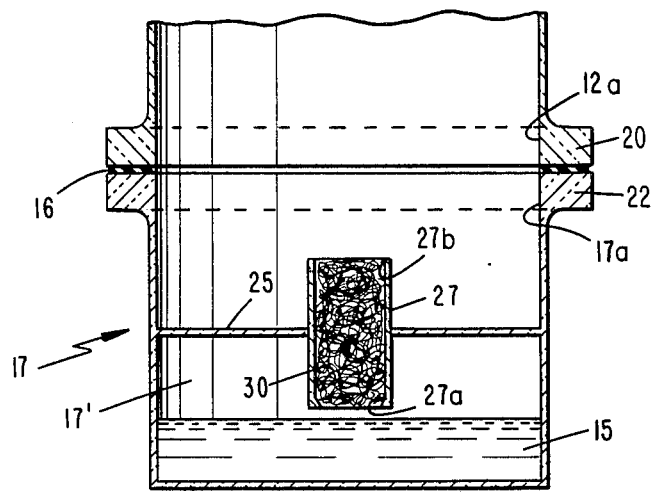
FIG. 3 is a cross-sectional view of a lower container containing a saturated salt solution utilized in the present invention.

Reference will now be made in detail to the present preferred embodiment of the invention, an example of which is illustrated in the accompanying drawings. FIG. 1 represents one embodiment of an improved humidification apparatus 10 of the invention comprising a bell-jar-shaped glass container 12 having an interior volumetric test region 14 into which test specimens may be suspended utilizing appropriate glass specimen holders, hooks, or other support devices (not shown). The temperature within region 14 is controlled by placing apparatus 10 within a controllable oven. Humidity is maintained by use of saturated salt solution 15 disposed within a bottom container 17.

Container 12 is open at bottom 12a thereof while bottom container 17 is open at top 17a. Sealing flanges 20,22 provided respectively at the bottom and top of containers 12,17 contact each other in sealing engagement to isolate test region 14 from ambient environment. Preferably, the mating surfaces of flanges 20,22 have disposed therebetween a sealing material, such as stopcock grease or a gasket 16 cut from an appropriate inert material so that no contamination from the gasket will be introduced into the test environment. Clamps (not shown) can be used to clamp flanges 20,22 together for improved sealing.

Bottom container 17 further includes a partition plate 25 separating saturated salt solution 15 from upper test region 14. A tube 27 passing through partition 25 has a lower end 27a disposed above the surface of solution 15 and an upper end 27b communicating with test region 14. Tube 27 provides communication between solution 15 and test region 14 so that gas humidified within a region 17' between the solution and partition plate flows through tube 27 into the test region to provide proper humidity levels at the chosen temperature.

Tube 27, as discussed above, provides a path permitting a flow of moist humid air upwards into bell jar container 12. Over prolonged testing time intervals, however, tube 27 may allow migration of salt particles from the solution 15 into the environmental test region 14. In the present invention, migration of salts is advantageously prevented by placement of a glass wool plug 30 within tube 27 that prevents passage of any liquids or solids upwards into test region 14 while allowing humidified air to flow upwards. Quartz wool is also acceptable, as is membranous material satisfying the foregoing function.

Migration of salt also tends to be impeded by mounting the tube 27 within partition 25 so that a lower portion of the tube and particularly lower end 27a is disposed below the partition. This arrangement increases the migration path salt particles would have to travel to reach test region 14 from bottom container 17.

Operation of humidification device 10 for environmental testing is as follows: The appropriate saturated salt solution 15 is poured through a funnel (not shown) resting within tube 27. Any stray salt or liquid is cleaned from the upper surfaces of partition 25 and the tube 27. Glass wool plug 30 is then inserted into tube 27 to restrict passage of all solids and liquids. An appropriate glass specimen holder (not shown) is placed upon the upper surface of partition 25 from which test specimens may be suspended from hooks within region 14. A proper gasket 16 or grease is then distributed on mating surfaces of flanges 20,22 with the flanges placed in sealing contact with each other and clamped together.

Glass stopcock 35 is open and the entire assembly is then placed into a temperature controlled oven for the environmental storage cycle. Apparatus 10 is allowed to reach the desired temperature so that humidity rises to the required level within container 12 as solution 15 releases water vapor and equilibrium of atmospheres within bottom container 17 and region 14 is obtained. Stopcock 35 is then closed and the humidity level is automatically maintained within region 14 for the time period desired.

The salt of which the saturated aqueous solution is prepared for use in the apparatus of this invention can be selected from a wide variety of salts. Examples of such salts include $KNO_2$, $Mg(NO_3)_2 \cdot 6H_2O$, $NaNO_2$, $NaClO_3$, $NH_4Cl$, $KBr$, $NH_4H_2PO_4$, $NaBr \cdot 2H_2O$, $NaCl$, $KHSO_4$, $NaNO_3$, $KCNS$, $KNO_3$, $CrO_3$, $KI$, $K_2CO_3 \cdot 2H_2O$, $Mg(CH_3COO)_2 \cdot 4H_2O$, $(NH_4)_2SO_4$ and $Na_2CO_3 \cdot 10H_2O$ and mixtures thereof. The manner in which the saturated aqueous solution is prepared and a discussion of these solutions generally can be found in U.S. Pat. No. 4,406,843 to Nakamura et al, the disclosure of which is hereby incorporated herein by reference in its entirety.

The foregoing description of the preferred embodiment of the invention has been presented for purposes of illustration and description. It is not intended to be exhaustive or to limit the invention to the precise form disclosed, and obviously many modifications and variations are possible in light of the above teachings. The embodiment was chosen and described in order to best explain the principles of the invention and its practical application to thereby enable others skilled in the art to best utilize the invention and various embodiments and with various modifications as are suited to the particular use contemplated. It is intended that the scope of the invention be defined by the claims appended hereto.

What is claimed is:

1. A device for maintaining and controlling the humidity of a gas within a sealed environment, comprising container means having a partition for separating the interior of said container means into upper and lower chambers, said lower chamber containing an aqueous saturated salt solution containing crystals of said salt, a tube extending through the partition plate to provide communication between said upper and lower chambers and to enable gas humidified by the salt solution within the lower chamber to pass into the upper chamber; and further including means for preventing salt from said salt solution from migrating to the upper chamber from the lower chamber, said salt migration preventing means being located within said tube.

2. The device of claim 1, wherein said salt migration preventing means comprises a glass wool plug.

3. The device of claim 1, wherein said salt migration preventing means comprises a membrane having sufficient porosity to allow moist air to pass therethrough while preventing salts from entering the upper chamber.

4. The device of claim 3, wherein said tube extends below a lower surface of said partition plate so that a lower end of said tube is located below the partition plate and above the surface of said salt solution.

5. The device of claim 1, wherein said container means includes a first container open at the bottom and a second container open at the top, said second container including said partition plate and tube, said first and second containers each further including a flange engageable with each other when said first container is mounted on said second container.

6. The device of claim 5, further including sealing material disposed between said flanges.

7. The device of claim 6, wherein said sealing material is grease.

8. The device of claim 5, further including means for clamping said flanges together.

9. The device of claim 5, wherein said first container is a bell-shaped jar.

10. The device of claim 9, wherein said first container includes a stopcock.

* * * * *